US012758309B2

(12) United States Patent
Amit et al.

(10) Patent No.: US 12,758,309 B2
(45) Date of Patent: Oct. 13, 2026

(54) SYSTEMS AND METHODS FOR RECOMMENDING ABLATION LINES

(71) Applicant: BIOSENSE WEBSTER (ISRAEL) LTD., Yokneam (IL)

(72) Inventors: Matityahu Amit, Cohav-Yair Zur-Yigal (IL); Yariv Avraham Amos, Tzorit (IL); Liat Tsoref, Tel Aviv (IL); Stanislav Goldberg, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 577 days.

(21) Appl. No.: 18/207,854

(22) Filed: Jun. 9, 2023

(65) Prior Publication Data

US 2023/0397950 A1 Dec. 14, 2023

Related U.S. Application Data

(60) Provisional application No. 63/350,983, filed on Jun. 10, 2022.

(51) Int. Cl.
*A61B 18/14* (2006.01)
*G16H 50/20* (2018.01)
*A61B 18/00* (2006.01)

(52) U.S. Cl.
CPC ......... *A61B 18/1492* (2013.01); *G16H 50/20* (2018.01); *A61B 2018/00351* (2013.01); *A61B 2018/00577* (2013.01); *A61B 2018/00839* (2013.01)

(58) Field of Classification Search
CPC ...... A61B 18/1492; A61B 2018/00351; A61B 2018/00577; A61B 2018/00839; G16H 50/20
See application file for complete search history.

(56) References Cited

U.S. PATENT DOCUMENTS 11,198,004 B2 12/2021 Garner
2014/0296842 A1* 10/2014 Mansi .................... A61B 34/10 703/2
2019/0259493 A1* 8/2019 Xu ......................... G16H 30/40
(Continued)

FOREIGN PATENT DOCUMENTS

WO WO-2013123549 A1 * 8/2013 ............. A61B 5/349
WO WO-2021062366 A1 * 4/2021 ............. G16B 40/20

OTHER PUBLICATIONS

Bianchi et al., "Graph Neural Networks with Convolutional ARMA Filters", IEEE Transactions on Pattern Analysis and Machine Intelligence, vol. 44, pp. 3496-3507, 2019.
(Continued)

*Primary Examiner* — Joanne M Rodden
*Assistant Examiner* — Bo Ouyang
(74) *Attorney, Agent, or Firm* — Clayton, McKay & Bailey, PC

(57) ABSTRACT

A system for improving a cardiac ablation procedure includes a recommendation unit configured to provide an initial recommendation for at least one proposed ablation line for an ablation procedure on an anatomy of a patient. The system displays the at least one proposed ablation line on an anatomical map of the anatomy. The recommendation unit comprises a first and a second trained machine-learning model. Both the first and second trained machine-learning models have the same structure.

18 Claims, 7 Drawing Sheets

(56) References Cited

U.S. PATENT DOCUMENTS

| | | | |
|---|---|---|---|
| 2020/0022649 A1* | 1/2020 | Rodriguez | ........... A61B 5/4878 |
| 2020/0352652 A1 | 11/2020 | Amit et al. | |
| 2021/0137384 A1 | 5/2021 | Robinson et al. | |
| 2022/0036560 A1 | 2/2022 | Amos et al. | |

OTHER PUBLICATIONS

Gasteiger et al., "Predict then Propagate: Graph Neural Networks meet Personalized PageRank", International Conference on Learning Representations, 13 pages, Oct. 14, 2018.
Kaiming et al., "Identity Mappings in Deep Residual Networks", European Conference on Computer Vision, 15 pages, 2016.
Tang et al, "Dense Graph Convolutional Neural Networks on 3D Meshes for 3D Object Segmentation and Classification" Image and Vision Computing, vol. 114, 12 pages, Oct. 1, 2021.
International Search Report for corresponding PCT Appln. No. PCT/IB2023/056006 dated Sep. 18, 2023.
Kaba, R. A., Momin, A. & Camm, J. Persistent atrial fibrillation: The role of left atrial posterior wall isolation and ablation strategies. J. Clin. Med. 10, (2021).
Breiman L(2001)."Random Forests". Machine Learning. 45 (1): 5-32, 2001.
Ho, Tin Kam (1995).Random Decision Forests, Proceedings of the 3rd International Conference on Document Analysis and Recognition, Montreal, QC, Aug. 14-16, 1995. pp. 278-282.
Cortes, Corinna; Vapnik, Vladimir (1995), "Support-vector networks" , Machine Learning. 20 (3):273-297.

* cited by examiner

SYSTEMS AND METHODS FOR RECOMMENDING ABLATION LINES

CROSS REFERENCE TO RELATED APPLICATIONS

This application claims priority from U.S. provisional patent application 63/350,983, filed Jun. 10, 2022, which is incorporated herein by reference.

FIELD OF THE INVENTION

The present invention relates to systems for treatment of atrial fibrillation generally.

BACKGROUND OF THE INVENTION

Atrial fibrillation (AF) is the most common diagnosed sustained arrhythmia and is characterized by rapid and irregular activation of the atria. Atrial fibrillation can be paroxysmal, lasting 7 days or less with or without intervention, or may be continuous beyond 7 days (persistent, PS-AF) or beyond 12 months (long-standing, LS-PS-AF). Permanent AF is the term used for long-standing persistent AF when any attempt to restore sinus rhythm has been abandoned or has proved impossible. (See e.g., Kaba, R. A., Momin, A. & Camm, J. Persistent atrial fibrillation: The role of left atrial posterior wall isolation and ablation strategies. J. Clin. Med. 10, (2021).

Treatment strategies vary depending on the extent and duration of AF. As an example, paroxysmal AF is typically managed with wide antral circumferential ablation (WACA), i.e., providing radiofrequency energy in a point-by-point fashion along pre-defined lines of the atrium. However, a large proportion of patients with AF have PS-AF or LS-PS-AF, which are more difficult to treat, likely due to a wider spread of arrhythmogenic triggers and substrates outside of the pulmonary veins. The posterior wall of the left atrium is a common site for these changes and has become a target of ablation strategies to treat these more resistant forms of AF. Other common sites are the left and right carina and roof.

SUMMARY OF THE PRESENT INVENTION

There is therefore provided, in accordance with a preferred embodiment of the present invention, a system for improving a cardiac ablation procedure which includes a recommendation unit. The recommendation unit provides an initial recommendation for at least one proposed ablation line for an ablation procedure on an anatomy of a patient and displays the at least one proposed ablation line on an anatomical map of the anatomy. The recommendation unit includes a first and a second trained machine-learning model, both of which have the same structure.

Moreover, in accordance with a preferred embodiment of the present invention, the system includes an ablation line editor which enables a physician to modify a selected one of the at least one proposed ablation line.

Further, in accordance with a preferred embodiment of the present invention, the system includes a treatment determiner which determines a recommended energy delivery per segment of a chosen ablation line.

Still further, in accordance with a preferred embodiment of the present invention, the system includes a guidance unit which displays a next ablation site on the anatomy based at least on a chosen ablation line and on a catheter location in the anatomy.

Moreover, in accordance with a preferred embodiment of the present invention, the recommendation unit includes a map segmenter, an ablation line trainer and an ablation line proposer. The map segmenter segments the anatomical map to output parts of the anatomy, the map segmenter utilizing the first trained machine-learning model. The ablation line trainer trains the second trained machine-learning model to output proposed ablation lines. The ablation line proposer utilizes the second trained machine-learning model to propose the at least one proposed ablation line for the anatomy.

Further, in accordance with a preferred embodiment of the present invention, the same structure is a graph convolutional neural network (GCN) or a classifier.

Still further, in accordance with a preferred embodiment of the present invention, the recommendation unit recommends which one of the at least one proposed ablation line is most suitable for a procedure for the patient.

Moreover, in accordance with a preferred embodiment of the present invention, the at least one proposed ablation line is a wide antral circumferential ablation (WACA) line.

Further, in accordance with a preferred embodiment of the present invention, the system includes a key point falterer to compare actual ablation points of a training case to intersection points or lines of neighboring parts on a segmented map of the training case and to select those ablation points closest to the intersection points as key points.

There is also provided, in accordance with a preferred embodiment of the present invention, a computer-implement method for improving a cardiac ablation procedure. The method includes providing an initial recommendation for at least one proposed ablation line for an ablation procedure on an anatomy of a patient. The providing includes displaying the at least one proposed ablation line on an anatomical map of the anatomy. The initial recommendation utilizes a first and a second trained machine-learning model both of which have the same structure.

Moreover, in accordance with a preferred embodiment of the present invention, the method includes enabling a physician to modify a selected one of the at least one proposed ablation line.

Further, in accordance with a preferred embodiment of the present invention, the method includes determining a recommended energy delivery per segment of a chosen ablation line.

Still further, in accordance with a preferred embodiment of the present invention, the method includes displaying a next ablation site on the anatomy based at least on a chosen ablation line and on a catheter location in the anatomy.

Moreover, in accordance with a preferred embodiment of the present invention, the providing includes segmenting the anatomical map to output parts of the anatomy, the segmenting utilizing the first trained machine-learning model, training the second trained machine-learning model to output proposed ablation lines, and proposing the at least one proposed ablation line for the anatomy, the proposed utilizing the second trained machine-learning model.

Further, in accordance with a preferred embodiment of the present invention, the same structure is a graph convolutional neural network (GCN) or a classifier.

Still further, in accordance with a preferred embodiment of the present invention, the providing comprises recommending which one of the at least one proposed ablation lines is most suitable for a procedure for the patient.

Moreover, in accordance with a preferred embodiment of the present invention, the at least one proposed ablation line is a wide antral circumferential ablation (WACA) line.

Finally, in accordance with a preferred embodiment of the present invention, the method includes comparing actual ablation points of a training case to intersection points or lines of neighboring parts on a segmented map of the training case and selecting those ablation points closest to the intersection points as key points.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
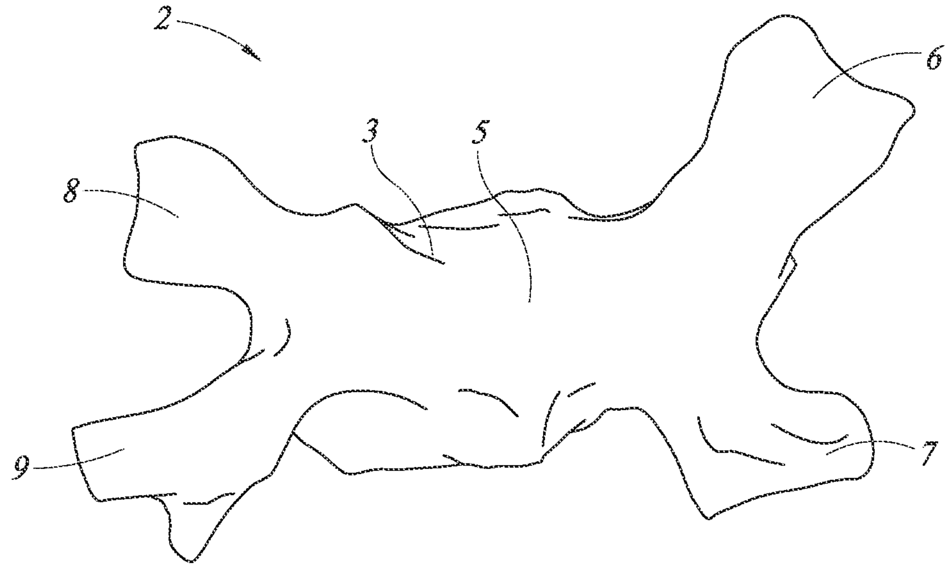
FIGS. 1A and 1B are schematic illustrations of an exemplary left atrium in the posterior anterior view, respectively without and with ablation lines marked thereon.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of one example of the invention. However, it will be understood by those skilled in the art that the present invention may be practiced within the scope of the amended claims in myriad other examples or embodiments without conforming with the specific details of the particular illustrative example provided herein. In other instances, well-known methods, procedures, and components have not been described in detail so as not to obscure the present invention.

Applicant has realized that deep learning systems may be utilized for planning ablation lines, such as wide antral circumferential ablation (WACA) lines and for checking how close the lines actually performed on the left atrium are to the planned ones. In addition, Applicant has realized that the problem of defining ablation lines is a segmentation problem. Thus, the input to such a system may be an anatomical map of the patient's heart and that the same type of deep learning structure may be utilized both for automatically segmenting the anatomical map as well as for defining the locations of the ablation lines.

Figure 1B:
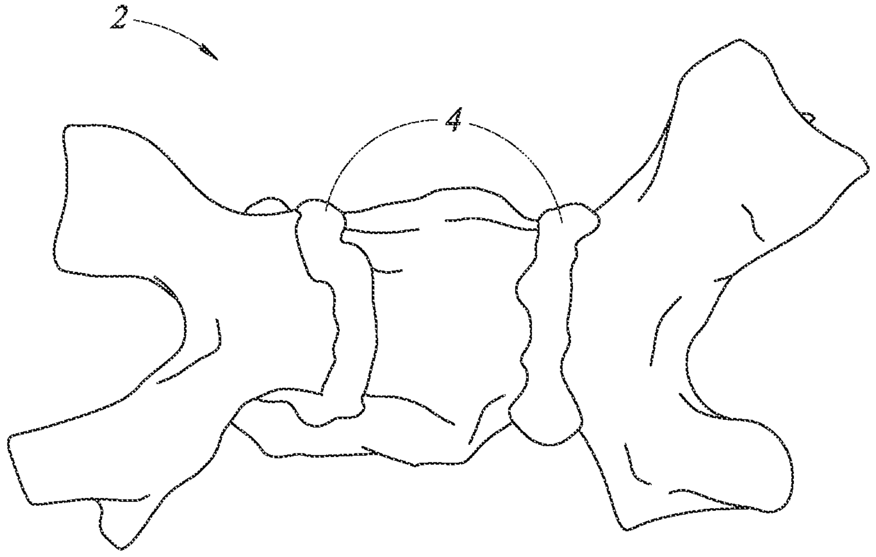

Reference is now made to FIG. 1A, which illustrates an exemplary left atrium 2 in the posterior anterior (PA) view, and to FIG. 1B, which illustrates exemplary ablation lines 4 marked on left atrium 2. Left atrium 2 has multiple areas, such as a roof wall 3, and a posterior wall 5. To its right, is a right superior pulmonary vein (RSPV) 6 and a right inferior PV (RIPV) 7, and to its left is a left inferior PV (LIPV) 8 and a left superior PV (LSPV) 9.

Figure 2:
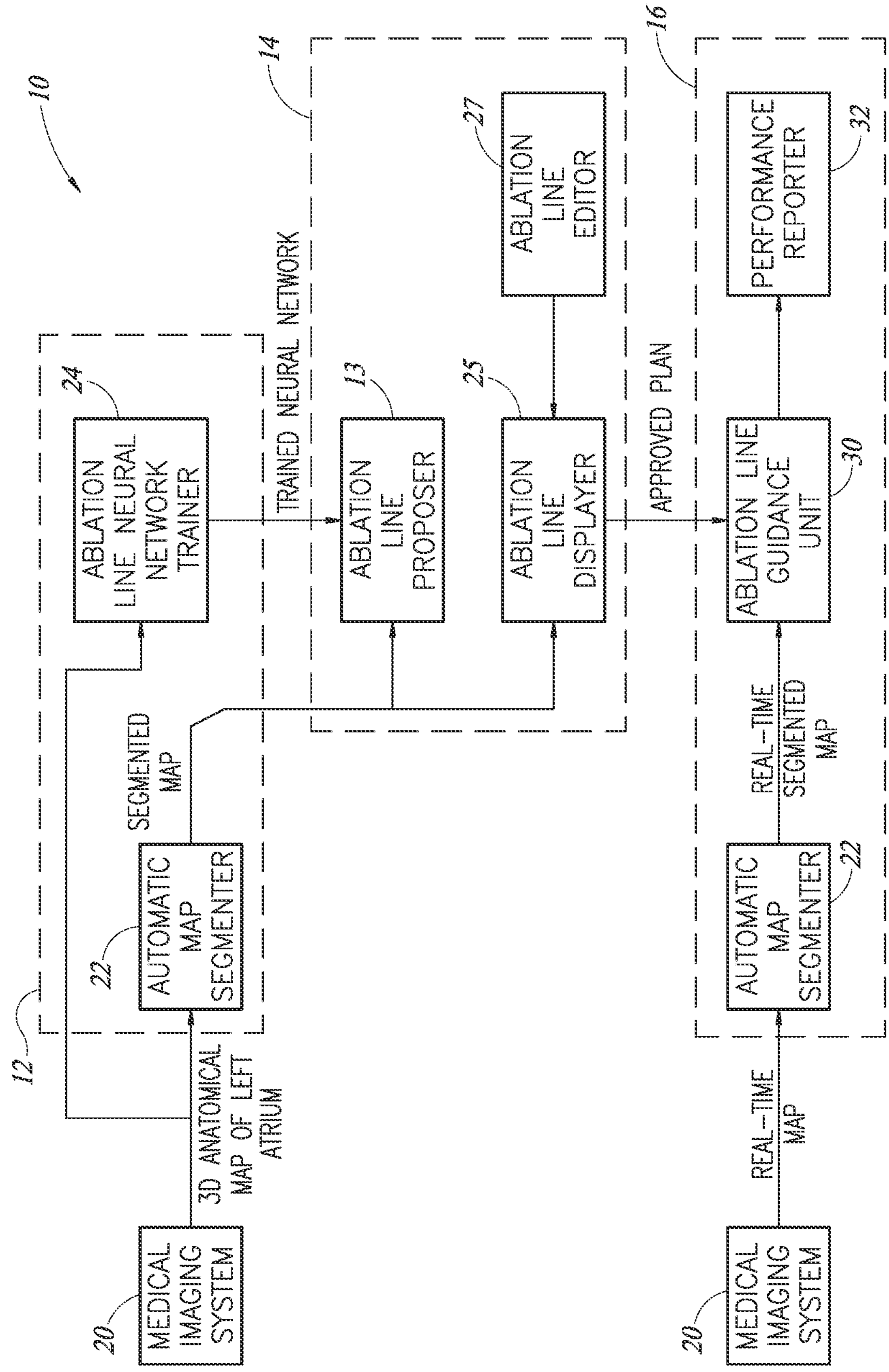
FIG. 2 is a block diagram illustration of a deep learning system for rendering recommended ablation line(s) on an anatomy, constructed and operative in accordance with a preferred embodiment of the present invention.

Reference is now made to FIG. 2, which illustrates a deep learning system 10 for rendering recommended ablation line(s) on an anatomy. Deep learning system 10 comprises three sections, an ablation line trainer 12 which builds a trained deep learning unit for an ablation line proposer 13, an ablation line recommender 14 which generates ablation line recommendations using ablation line proposer 13, and an ablation line guider 16 which provides ablation line guidance during a procedure.

Ablation line trainer 12 may receive an anatomical map of the heart, which may be produced using an anatomical image produced by using a suitable medical imaging system 20, or using a fast anatomical mapping (FAM) technique available in the CARTO™ system, produced by Biosense Webster Inc. (Irvine, Calif), or using any other suitable technique, or using any suitable combination of the above. The map/model of the heart onto which the recommended ablation line(s) may be rendered may comprise any suitable type of three-dimensional (3D) anatomical map produced using any suitable technique. The map may come from an intracardial ECG (electrocardiogram) and may comprise both location information, of a catheter moving around the atrium, and ECG measurements, such as voltage at each location.

Ablation line trainer 12 may comprise an automatic map segmenter 22 to segment the 3D map of the heart received from imaging system 20 into its various parts, such as posterior and anterior walls, roof wall, inferior wall, left lateral, septum, mitral, left atrial appendage (LAA) and 4 pulmonary veins (LSPV, LIPV, RSPV, RIPV), and an ablation line neural network trainer 24 to investigate thousands of ablation cases on different maps received from imaging system 20, along with their different ablation strategies, to generate a trained deep learning unit for ablation line proposer 13.

Ablation line recommender 14, includes ablation line proposer 13, gives an initial recommendation for the typical ablation lines during a procedure, with the recommended line(s) being rendered on the anatomy, e.g., a model and/or anatomical map of the heart, segmented by automatic map segmenter 22, so that the physician may ablate as close as possible to the suggested line, thus yielding an ablation line that will be as close as possible to ablation lines preferred by key opinion leaders (KOLs) in the field. It is noted however that ablation line proposer 13 may display the recommended ablation lines described herein with an ablation line displayer 25 on any digital depiction of the anatomy, whether an anatomical map or ultrasound imagery, including 4D ultrasound imagery, or the like. Accordingly, as used herein, a "map" of anatomy refers to any such digital depiction onto which an ablation line may be projected.

Ablation line proposer 13 may allow the physician to specify the required ablation lines; which may be known ablation lines such as e.g.: WACA, roofline, carina lines (right, left), posterior line, anterior line, inferior line, mitral line, posterior wall debulking, anterior wall debulking, inferior wall debulking, left lateral debulking, LAA isolation, etc.

Ablation line recommender 14 may also comprise an ablation line editor 27 to enable the physician to review and modify the selected ablation line according to his or her requirements, preferences, and findings during the case. For example, a physician may want to edit the initial ablation lines such that it will contain triggers observed in the posterior wall.

Ablation line proposer 13 may segment WACA circles into sections and may recommend energy delivery per segment, i.e., the recommended ablation index (radiofrequency (RF) or irreversible electroporation (IRE)) and/or recommended distance between adjacent points, such as may be predefined for the particular ablation machine, such as the Carto™ machine, and/or may be configured by the physician prior to performing the ablation and/or may be per type of ablation line.

Ablation line editor 27 may also permit the physician to update the recommended treatment delivery per segment.

Ablation line recommender 14 may require the physician to approve the plan once he or she has reviewed all parameters.

Ablation line guider 16 provides ablation line guidance during a procedure. It may receive an anatomical map of the heart from medical imaging system 20 during the procedure and may comprise automatic map segmenter 22 to indicate the various elements of the heart during the procedure, an ablation line guidance unit 30 and a performance reporter 32.

During the procedure, based on the catheter location, and the related ablation line from the approved plan; ablation line guidance unit 30 may present a dynamic display of a next ablation site based on the previous site and on the recommended ablation line (approved or edited by the physician). The next ablation site may then be displayed based on a pre-defined distance e.g., 4 mm from the previous site, with a minimum distance from the suggested line and in the direction of advancement of the line.

The goal of an ablation procedure is to form effective lesions that can interrupt the abnormal electrical pathways causing arrhythmias. To this end, the ablation line guidance unit 30 may calculate an ablation index, indicating the quality of each radiofrequency (RF) ablation lesion during the procedure. The ablation index is a function of at least contact force, time, and power and thus, increases as an ablation operation continues. An instantaneous ablation index provides real-time feedback to the physician, enabling them to monitor and adjust their technique during the procedure.

Since the physician may define a "required ablation index" for a given ablation line and for a given segment within the line, ablation line guidance unit 30 may present both the "required ablation index" and the instantaneous ablation index of the current site. This may enable the physician to yield the desired ablation index.

Performance reporter 32 may provide a report to the physician based on his or her performance during the procedure with respect to the ablation plan produced by ablation line recommender 14. The report may include data such as, for example:

- Max and Median deviation from planned for each ablation line [in mm];
- The deviation from the planned location; including number and percentage of ablation points with distance of more (or less) than the planned distance; and
- The deviation from the ablation planned for each ablation line;

Note: this report may be particularly useful in training less experienced physicians.

Ablation line recommender 14 may be configured to always draw the recommended WACA (left and right) ablation lines.

Figure 3:
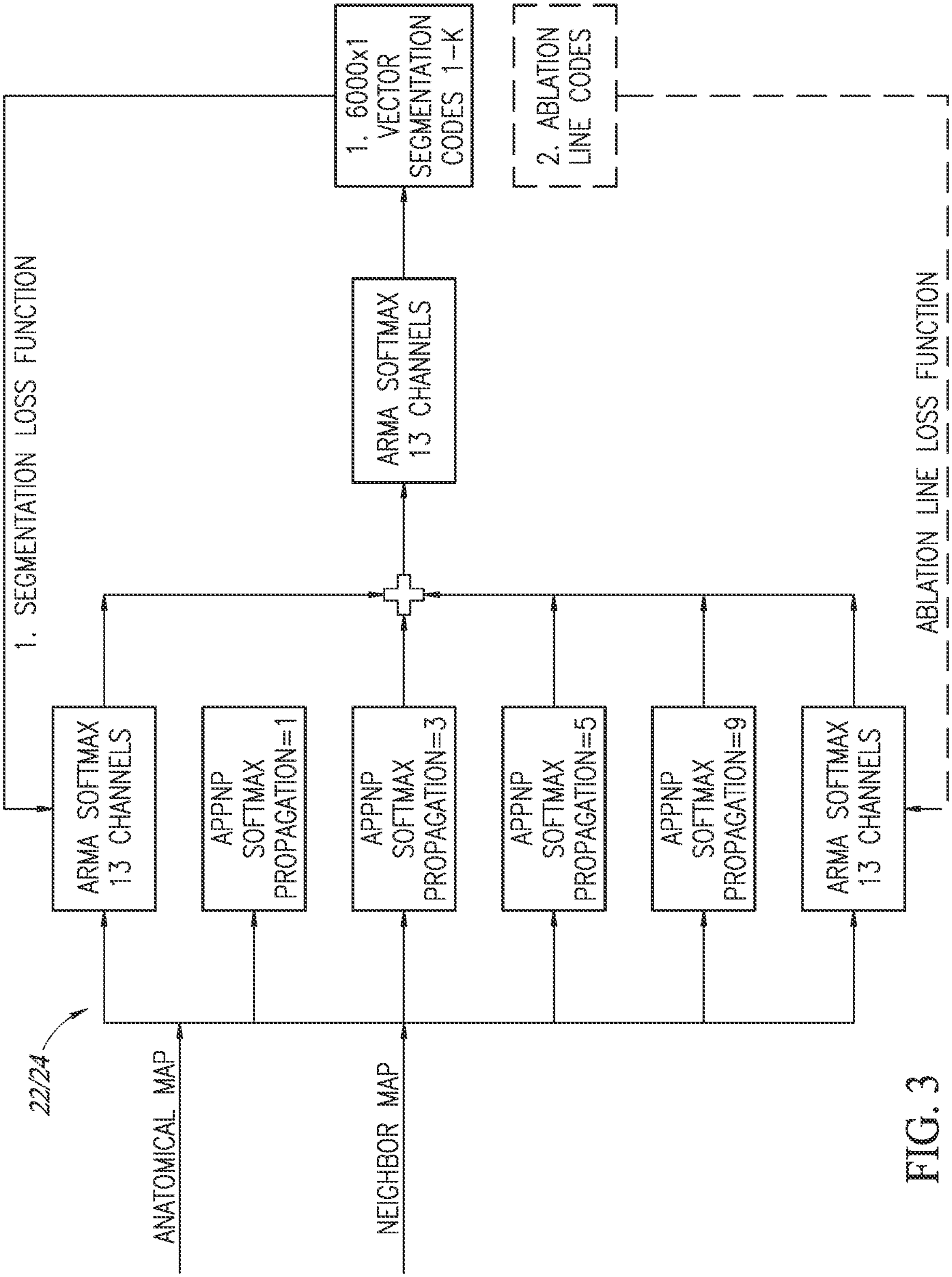
FIG. 3 is a block diagram illustration of a deep learning structure, useful in the system of FIG. 2.

As mentioned hereinabove, Applicant has realized that the same type of deep learning structure may be utilized and the same type of input provided to both automatic map segmenter 22 and ablation line neural network trainer 24. FIG. 3, to which reference is now made, shows the deep learning structure, discussed in more detail hereinbelow, and indicates that the input is the anatomical map, discussed above, and an adjacency map, discussed hereinbelow. FIG. 3, however, shows two types of output, segmentation codes for automatic map segmenter 22 and ablation line codes for ablation line neural network trainer 24.

Segmentation codes may be a set of codes indicating the parts of the heart, or the parts of the atria. For example, there may be 13 different parts of the atria. Ablation line codes may be a set of codes indicating a type of ablation line, as well as a code for all the areas which lack an ablation line. As discussed hereinbelow, each training case may comprise an input map and an output map with each location labeled with one of the relevant codes, a segmentation code for training automatic map segmenter 22 or an ablation line code for training ablation line neural network trainer 24.

The initial data set may be composed of a sufficient number of paroxysmal and persistent AF cases (e.g., 5000 or more cases) with anatomical maps of each case and at least one ablation line that was performed in that case. The ablation lines are typically one of the following: (1) left WACA, (2) right WACA, (3) ostial PVI, (4) roof line, (5) right carina, (6) left carina, (7) posterior line, (8) inferior line, (9) mitral isthmus line, (10) anterior line, (11) Cavo tricuspid isthmus (CTI) line, (12) Superior Vena Isolation (SVCI), (13) LAA isolation.

To prepare the initial data set to be used as input for training and testing automatic map segmenter 22 and ablation line neural network trainer 24, an expert physician (e.g., a KOL in the field) initially may add manual annotations of ablation points on the anatomical maps of the cases, as generated by imaging system 20. Each point is associated to at least one of the ablation lines (1)-(13).

Figure 4:
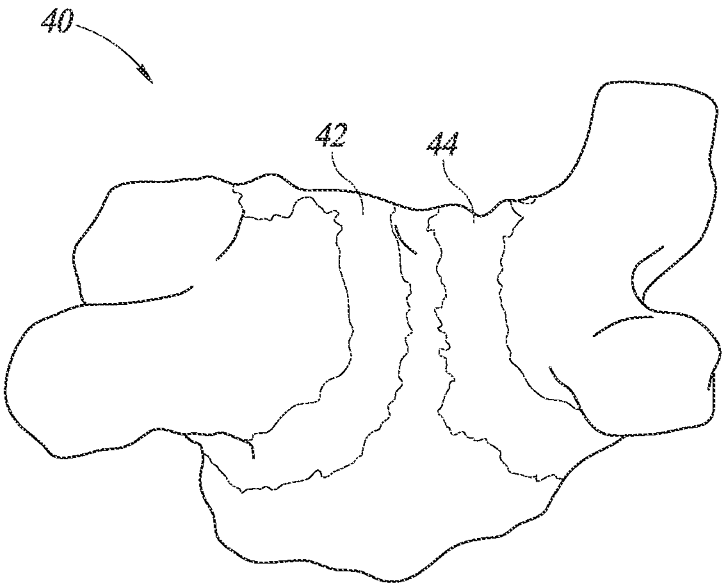
FIG. 4 is a schematic illustration of the exemplary left atrium of FIG. 1A with ablation lines thereon, useful in understanding the operation of the system of FIG. 2.

In a next step, data preprocessing may be performed whereby each ablation point may be rendered on the anatomical map using a particular radius (e.g., a 5 mm radius in this example). This is shown in FIG. 4, to which reference is now briefly made. FIG. 4 shows a posterior view of an exemplary left atrium 40 after projecting ablation points of 5 mm radius. FIG. 4 shows left WACA lines 42 and right WACA lines 44.

In another step, each map be investigated, and maps with gaps/or blurred lines may be filtered out from training and testing sets.

Following this, further data preprocessing may be performed in which:

a. The atrium is converted into a fixed dimension (e.g., by producing a constant mesh file with a fixed number of points, such as, for example, 2000 points and a 2000×

Figure 5:
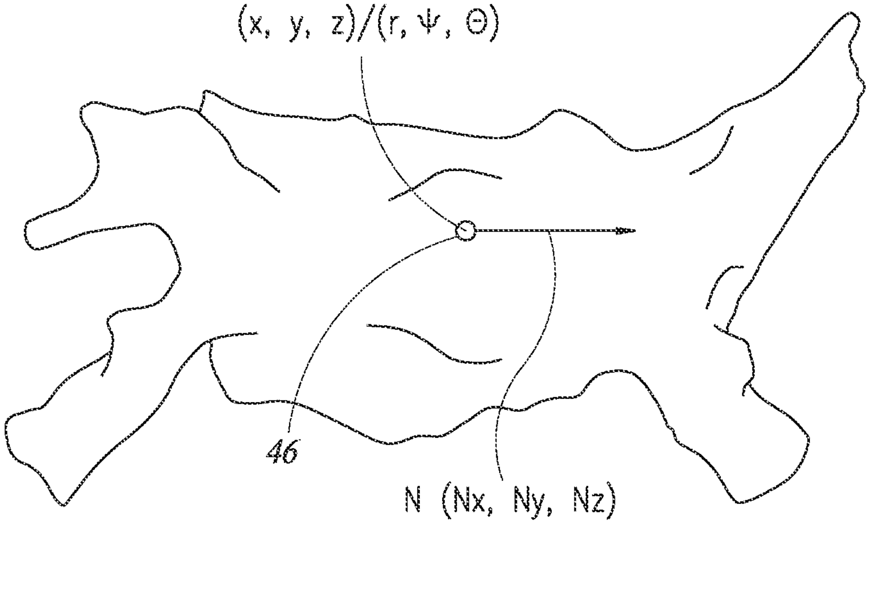
FIG. 5 is a schematic illustration of the exemplary left atrium of FIG. 1A with a point mesh face indicated thereon, useful in understanding the operation of the system of FIG. 2.

2000 adjacency matrix, where all values are configurable, such as values of 1000, 2000, 4000, 10000 etc.)

b. Feature extraction for 3D general segmentation: To build a deep learning framework for 3D segmentation, graph data is characterized by improving the local features of each node. This may be achieved utilizing 1-triangle neighborhood spatial and structural features of each mesh face, as depicted in FIG. 5, which shows a mesh face formed of a point 46, having a location (x, y, z) and a normal N to it, denoted by a vector (NX, Ny, Nz).

In a 1-triangle mesh, each face contains at most three adjacent faces. The 3D mesh structure data is characterized by M={V, E, F} of vertices, edges and face.

Therefore, the 1-triangle mesh is converted into a graph G={Features, Adjacency}. A face {F} on the mesh M has three corresponding nodes (vertices) on the graph {G}. The adjacency matrix {Adjacency} is a 6000×6000 matrix in our case. The adjacency matrix is based on {F} and represents the connections between vertices in M. In order to enhance the perception of the local area of the graph node, the spatial and structural geometric Features are used based on a single vertex of the simplified mesh (in this example composed of 6000 vertices). The feature space is a 6000×9 matrix, for each vertex (a triangle composed of three vertices with 3 adjacent faces), the pre-processing utilizes the following features:

$p_i$—the normalized ($x_i$, $y_i$, $z_i$) position of vertex Vi in the Euclidian space, where i represents the three indices of the vertices;

$sp_i$—spherical coordinate of vertex i ($\varphi_i$, $\theta_i$, $r_i$), where $\varphi_i$ is normalized by $\pi$ and $\theta$ is normalized by $2\pi$; and ni—normal of the vertex i defined by (xni, yni, zni).

c. Network Architecture: Automatic map segmenter 22 may utilize a machine-learning model composed of two layers, the first layer is composed of six graph convolutional neural network units, and the second layer is a decision layer comprised of another GCN with a Softmax unit. Each GCN unit gives a prediction of a given vertex to be associated to each one of the target categories (anatomical structures or ablation line).

As shown in FIG. 3, the anatomical map and the adjacency matrix serve as inputs to all units in the network. Two types of GCN units are used: 1) approximation personalized propagation of neural predictions (APPNP) and 2) auto regressive moving average layer (ARMA) that is highly efficient as a SoftMax layer for increasing the overall performance of the network during the training and cross validation stages and provides a more flexible frequency response, is more robust to noise, and better captures the global graph structure. Personalized graph neural networks are described by Gasteiger, J., Bojchevski, A. & Unnemann, S. G. Predict then propogate: Graph neural networks meet personalized PageRank. Int. Conf. Learn. Represent. (2018). Graph Neural networks with CNN ARMA filters have been described by Maria Bianchi, F., Grattarola, D., Livi, L. & Alippi, C. Graph Neural Networks with Convolutional ARMA Filters (2018). The APPNP unit models the relationship between GCN networks and the PageRank algorithm (a link analysis algorithm, originally designed by Google, which assigns a numerical weight to each node based on the quantity and quality of links point to it) and extends it to a personalized PageRank. It uses the information from a large, adjustable neighborhood for classifying each node. The model is computationally efficient and outperforms several state-of-the-art methods for semi-supervised classification on multiple graphs. The APPNP has 13 channels with a multi-layer perceptron (MLP) having two hidden layers with 128, and 64 neurons in each layer, respectively.

Figure 6:
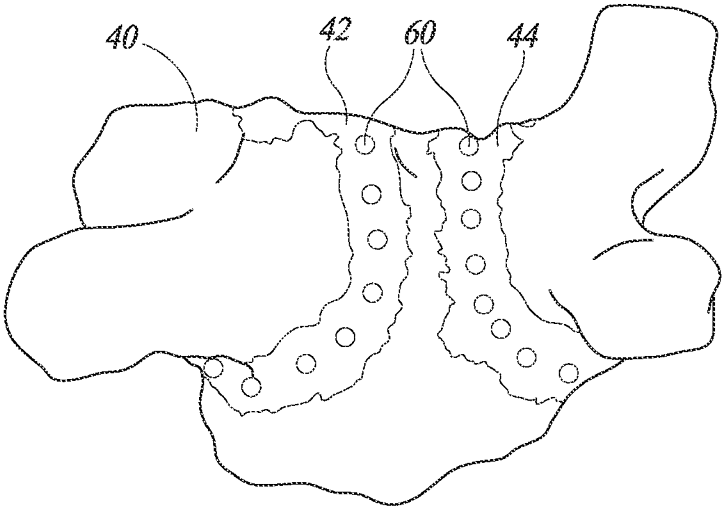
FIG. 6 is a schematic illustration of the exemplary left atrium of FIG. 1A with ablation points thereon, useful in understanding the operation of the system of FIG. 2.

The network weights are trained using a weighted category cross entropy loss function. Automatic map segmenter 22 may provide the segmentation codes to its segmentation loss function while ablation line neural network trainer 24 may provide the ablation line codes to its ablation line loss function.

d. In an exemplary embodiment, the training set contains 5000 maps. Each map is represented using three matrixes, a 6000×9 feature matrix, a 6000×6000 adjacency matrix and a 6000×1 target matrices, one for the segmentation codes and one for the ablation codes. For the ablation codes, zero represents no line while non-zero represents the ablation line ID.

e. Once the neural network of automatic map segmenter 22 is trained, automatic map segmenter 22 may segment the anatomical map of each atrium and may provide the segmented map to ablation line displayer 25.

f. From segmentation to line—Ablation line proposer 13 may create a centralized line with potential locations for point-by-point ablations on the anatomical map. For example, the map of FIG. 3 is depicted in FIG. 6 with the point-by-point ablations indicated by dots 50.

G. Point-by-point ablation “dots” may be updated on the fly based on actual ablation performed by the physician during each case. The mechanism for updating the dots may involve minimizing the distance between the planned line and the next dot in the direction of advancement of the ablation line.

As discussed, system 10 may use mapping data and automatic segmentation data to recommend which of the ablation lines is more suitable for a given case. The recommendation may be set based on indications from a specific research hospital or specific physicians (e.g., a KOL in the field of cardiac ablation) or based on data from a multitude of physicians and/or research hospitals.

In an alternative embodiment, the structure used for both automatic map segmenter 22 and ablation line trainer 24 may comprise a classifier operating on data of the intracardiac ECG. During intracardiac ECG recordings, catheters are inserted into the heart to measure the electrical activity of the heart. The per anatomical location the electrical signals are represented as voltage amplitude.

In this alternative embodiment, the classifier may be any suitable classifier, such as a Random Forest Classifier, a Support-Vector Machine (SVM) classifier or a deep learning classifier, such as are described in the following articles:

Breiman L (2001). “Random Forests”. Machine Learning. 45 (1): 5-32. Bibcode: 2001;

Ho, Tin Kam (1995). Random Decision Forests (PDF). Proceedings of the 3rd International Conference on Document Analysis and Recognition, Montreal, QC, 14-16 Aug. 1995. pp. 278-282. Archived from the original (PDF) on 17 Apr. 2016. Retrieved 5 Jun. 2016; and Cortes, Corinna; Vapnik, Vladimir (1995). “Support-vector networks” (PDF). Machine Learning. 20 (3): 273-297. CiteSeerX 10.1.1.15.9362. doi:10.1007/BF00994018. S2CID 206787478.

Each case in the training dataset may be preprocessed with an indication of whether one of given number of ablation lines (e.g., 14) were performed by a key opinion leader (KOL), so the target is a matrix of size N×14 where N represents the number of cases in the training dataset.

iii. Input Data: ECG data from the intracardiac ECG is saved as an additional feature matrix of 6000×22. The following triggers and substrate maps from the intracardiac ECG data are used as feature spaces:

1) "Finder" Focal source per vertex (6000×1) represents a number of S-waves per second;
2) "Finder" RAP—each vertex is represented by a number of rotational patterns per second;
3) CL—Cycle Length mapping—each vertex is represented by a cycle length in msec;
4) STD CL— Cycle length standard deviation—each vertex is represented by a cycle length standard deviation per second;
5) Spatial temporal dispersion—each vertex represents a percentage of spatial temporal dispersion (out of 10-30 second of the recording);
6) Periodic Spatial temporal dispersion—each vertex represents a percentage of periodic spatial temporal dispersion (out of 10-30 second of the recording);
7) Voltage Map—each vertex represents a bipolar amplitude in mV;
8) CLM ROI—each vertex represents an existence of cycle length region of interest, based on a cutoff of cycle length<minimum CL+15 msec and STD CL<15 msec;
9) Segmentation hot one encoding is the output of automatic map segmenter 22: a matrix of size (6000×K) where K represents the number of anatomical structures (13 for the LA), (output from segmentation algorithm). Ablation line encoding is the output of ablation line trainer 24;
10) Global voltage per segmentation region (6000×1) mV; and
11) Low voltage zone areas which are regions within the left atria where the recorded voltage amplitudes are relatively low compared to surrounding areas. For example, these may be areas whose voltages are between 0.2-0.5 mV. Typically, a scar may be defined as an area whose voltage is below 0.2 mV. It will be appreciated that these thresholds may differ based on operator decision in the procedure.

The classifier may receive a feature matrix as input, which may have dimensions of 6000×M, where 6000 represents the number of vertices on the map, and M represents the number of features (focal, substrate related, ripple, frequency, anatomical location, etc.).

The target vector has dimensions of K×1, where K indicates the number of ablation approaches or IDs. For this embodiment, the data may be from successful cases of the procedure, specifically those with a 12-month freedom from any arrhythmia. For each of these cases, the K×1 vector will be set to 1 if a particular ablation approach was performed during the procedure.

The neural networks of the classifier may utilize a set of dense nets, where the last layer will consist of a SoftMax layer with K neurons in the output layer. This modification enables the prediction of the K ablation approaches.

It will be appreciated that the systems and methods described herein may be in various local or distributed computers (e.g., a cloud-based processing systems) including but not limited to the form described by U.S. Pat. No. 11,198,004 or US Patent Publication No. 20200352652A1, owned by Applicant and incorporated herein by reference.

Figure 7:
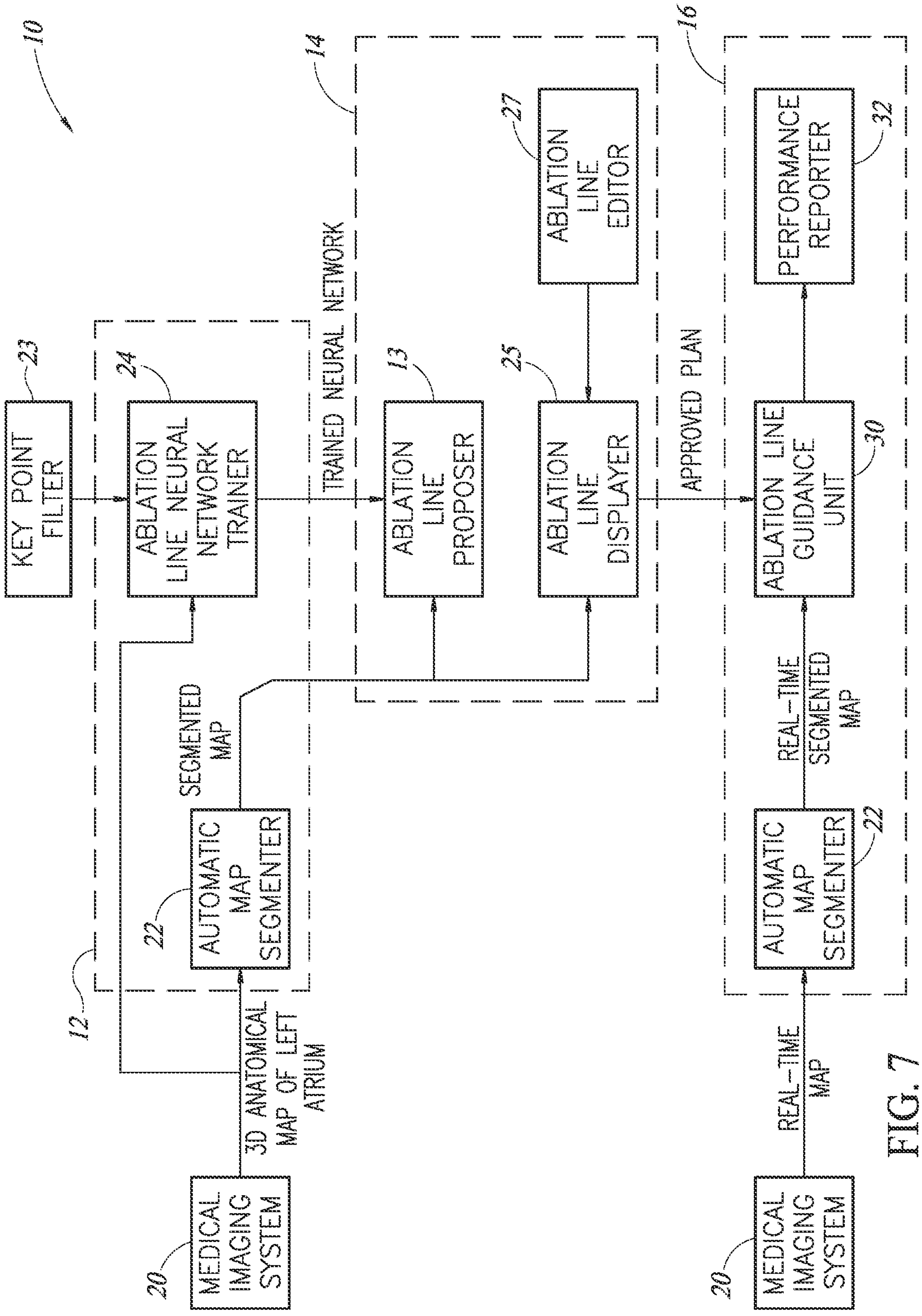
FIG. 7 is a block diagram illustration of an alternative deep learning system for rendering recommended ablation line(s) on an anatomy, constructed and operative in accordance with an alternative preferred embodiment of the present invention.
Figure 8:
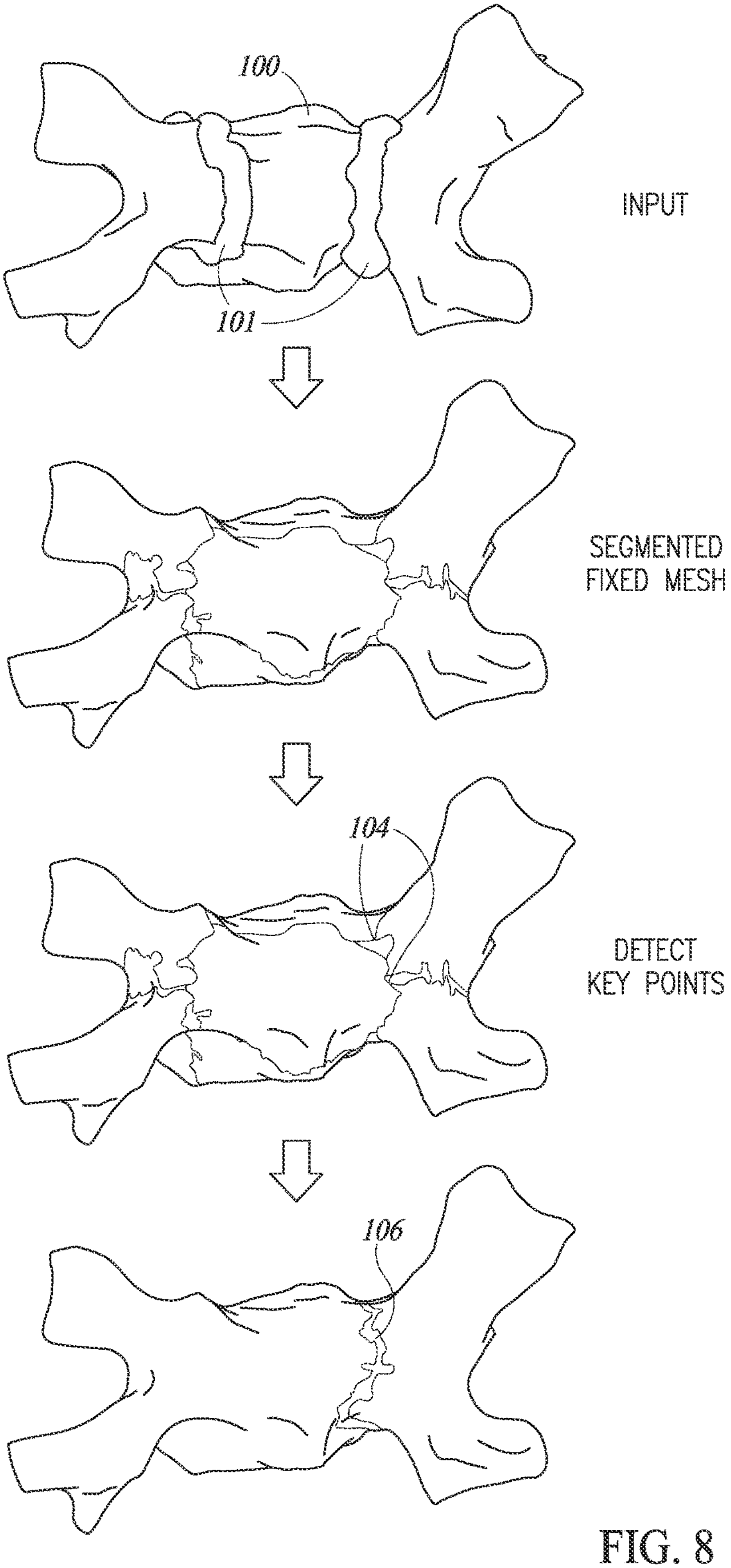
FIG. 8 is a schematic illustration of the operation of a key point falterer, useful in the system of FIG. 7.

Applicant has realized that actual ablation line data may be noisy and the ablation lines they indicate may not be the ideal lines. In another embodiment, shown in FIG. 7 to which reference is now made, system 10' may additionally comprise a key point filterer 23 to review the noisy ablation line data and, based on the segmentation map received from automatic map segmenter 22, may find those ablation points in the ablation line data which may be defined as key points (i.e., the important points along the ablation line which should not have been missed) as defined by an expert, such as a KOL, associated with it. Typically, these key points may be points at the intersection of two parts of the atrium. This is shown in FIG. 8, to which reference is now made. The input 100 to key point filterer 23 may be an image or a mesh of the left atrium with the actual ablation lines, which may have been segmented (102) by automatic map segmenter 22. Key point filterer 23 may detect the key points 104 by comparing the ablation points of each case to the intersection points on the segmented map 102 for that case and selecting those ablation points closest to the intersection points. Key point filterer 23 may combine key points from multiple cases to generate resultant ablation lines 106 for training which may be thinner and better defined than otherwise. Key point filterer 23 may provide the resultant ablation lines 106 to ablation line neural network trainer 24 for training.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a client/server system, mobile computing devices, smart appliances, cloud computing units or similar electronic computing devices that manipulate and/or transform data within the computing system's registers and/or memories into other data within the computing system's memories, registers or other such information storage, transmission or display devices.

Embodiments of the present invention may include apparatus for performing the operations herein. This apparatus may be specially constructed for the desired purposes, or it may comprise a computing device or system typically having at least one processor and at least one memory, selectively activated or reconfigured by a computer program stored in the computer. The resultant apparatus when instructed by software may turn the general-purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus. The computer readable storage medium may also be implemented in cloud storage.

Some general-purpose computers may comprise at least one communication element to enable communication with a data network and/or a mobile communications network.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A system for improving a cardiac ablation procedure, the system comprising:

a recommendation unit configured to provide an initial recommendation for at least one proposed ablation line for an ablation procedure on an anatomy of a patient, said system displaying said at least one proposed ablation line on an anatomical map of said anatomy;

wherein the recommendation unit comprises:

a first trained machine-learning model configured to segment the anatomical map;

a second trained machine-learning model configured to propose the at least one proposed ablation line based, at least in part, on one or more segments output from the first trained machine-learning model; and a key point filterer configured to compare actual ablation points of a training case to intersection points or lines of neighboring parts on a segmented map of said training case and to select the actual ablation points closest to said intersection points or lines as key points, wherein both said first and second trained machine-learning models have a same structure.

2. The system of claim 1 further comprising an ablation line editor configured to enable a physician to modify a selected one of said at least one proposed ablation line.

3. The system of claim 1 further comprising a treatment determiner configured to determine a recommended energy delivery per segment of a chosen ablation line.

4. The system of claim 1 further comprising a guidance unit to display a next ablation site on said anatomy based at least on a chosen ablation line and on a catheter location in said anatomy.

5. The system of claim 1 and wherein said recommendation unit comprises:

a map segmenter to segment said anatomical map to output parts of said anatomy, said map segmenter utilizing said first trained machine-learning model;

an ablation line trainer to train said second trained machine-learning model to output proposed ablation lines; and an ablation line proposer utilizing said second trained machine-learning model to propose said at least one proposed ablation line for said anatomy.

6. The system according to claim 5, wherein said same structure is a graph convolutional neural network (GCN).

7. The system according to claim 5, wherein said same structure is a classifier.

8. The system according to claim 1 wherein the recommendation unit is further configured to recommend which one of the at least one proposed ablation line is most suitable for a procedure for said patient.

9. The system according to claim 1 wherein said at least one proposed ablation line is a wide antral circumferential ablation (WACA) line.

10. A computer-implemented method for improving a cardiac ablation procedure, the method comprising:

providing an initial recommendation for at least one proposed ablation line for an ablation procedure on an anatomy of a patient, comprising displaying said at least one proposed ablation line on an anatomical map of said anatomy;

wherein the initial recommendation utilizes:

a first trained machine-learning model configured to segment the anatomical map;

a second trained machine-learning model configured to propose the at least one proposed ablation line based, at least in part, on one or more segments output from the first trained machine-learning model; and a key point filterer configured to compare actual ablation points of a training case to intersection points or lines of neighboring parts on a segmented map of said training case and to select the actual ablation points closest to said intersection points or lines as key points, wherein both said first and second trained machine-learning models have a same structure.

11. The method of claim 10 further comprising enabling a physician to modify a selected one of said at least one proposed ablation line.

12. The method of claim 10 further comprising determining a recommended energy delivery per segment of a chosen ablation line.

13. The method of claim 10 further comprising displaying a next ablation site on said anatomy based at least on a chosen ablation line and on a catheter location in said anatomy.

14. The method of claim 10 and wherein said providing comprises:

segmenting said anatomical map to output parts of said anatomy, said segmenting utilizing said first trained machine-learning model;

training said second trained machine-learning model to output proposed ablation lines; and proposing said at least one proposed ablation line for said anatomy, said proposed utilizing said second trained machine-learning model.

15. The method according to claim 14, wherein said same structure is a graph convolutional neural network (GCN).

16. The method according to claim 14, wherein said same structure is a classifier.

17. The method according to claim 10 wherein providing further comprises recommending which one of the at least one proposed ablation lines is most suitable for a procedure for said patient.

18. The method according to claim 10 wherein said at least one proposed ablation line is a wide antral circumferential ablation (WACA) line.

* * * * *